United States Patent [19]

Umemura et al.

[11] 4,217,309
[45] Aug. 12, 1980

[54] PROCESS FOR PRODUCING METHACROLEIN

[75] Inventors: Sumio Umemura; Kyoji Ohdan; Kenichi Suzuki; Yasuo Bando; Terumi Hisayuki, all of Ube, Japan

[73] Assignee: Ube Industries, Ltd., Yamaguchi, Japan

[21] Appl. No.: 15,903

[22] Filed: Feb. 28, 1979

[30] Foreign Application Priority Data

Jun. 12, 1978 [JP] Japan .................................. 53-69832
Oct. 25, 1978 [JP] Japan ................................. 53-130475

[51] Int. Cl.² ............................................ C07C 45/04
[52] U.S. Cl. ................................ 568/477; 252/466 R; 568/478; 568/479
[58] Field of Search ..................... 260/604 R; 252/466

[56] References Cited

U.S. PATENT DOCUMENTS

| | | | |
|---|---|---|---|
| 3,600,443 | 8/1971 | Cevidallis et al. | 260/604 R |
| 3,825,502 | 7/1974 | Takenaka et al. | 260/604 R |
| 3,966,823 | 6/1976 | Takenaka et al. | 260/604 R |
| 4,001,317 | 1/1977 | Grasselli et al. | 260/604 R |
| 4,049,577 | 9/1977 | Childress et al. | 260/604 R |
| 4,111,985 | 9/1978 | Okada et al. | 260/604 R |

FOREIGN PATENT DOCUMENTS

| | | | |
|---|---|---|---|
| 947772 | 5/1974 | Canada | 260/604 R |
| 47-42813 | 10/1972 | Japan | 260/604 R |
| 48-17253 | 5/1973 | Japan | 260/604 R |
| 48-52713 | 7/1973 | Japan | 260/604 R |
| 51-34107 | 3/1976 | Japan | 260/604 R |
| 51-47684 | 12/1976 | Japan | 260/604 R |

Primary Examiner—Werren B. Lone
Attorney, Agent, or Firm—Burgess, Ryan and Wayne

[57] ABSTRACT

Methacrolein is produced in a high yield by catalytically oxidizing isobutylene at a temperature of from 250° to 500° C. by using a catalyst represented by the formula:

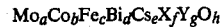

$$Mo_aCo_bFe_cBi_dCs_eX_fY_gO_h$$

wherein X is either both vanadium and palladium, Y is at least one member selected from titanium, nickel, tin and zirconium, a=12, b=2-12, c=0.5-7, d=0.1-5, e=0.0005-0.5, f=0.01-2, g=0-5 and h is a positive number proportional to the number of oxygen atoms satisfying the average valency of the metal atoms stated in the formula, which catalyst has a high resistance to compression and abrasion and exhibits a high catalytic efficiency, mechanical strength and durability.

10 Claims, No Drawings

PROCESS FOR PRODUCING METHACROLEIN

FIELD OF THE INVENTION

The present invention relates to a process for producing methacrolein by the catalytic oxidation of isobutylene in a vapor phase with molecular oxygen at an elevated temperature. More particularly, the present invention relates to a process for producing methacrolein by the catalytic oxidation of isobutylene in a vapor phase with molecular oxygen at an elevated temperature by using a new type of catalyst having a more enhanced catalytic activity, durability and mechanical strength than those of conventional catalysts containing molybdenum, bismuth, iron, cobalt and an alkali metal as catalytic ingredients.

BACKGROUND OF THE INVENTION

Known are various types of processes for producing unsaturated aliphatic aldehydes such as acrolein and methacrolein by the catalytic oxidation of olefins such as propylene and isobutylene in a vapor phase with molecular oxygen at an elevated temperature. Also, various types of catalysts effective for the above-mentioned processes are known. In connection with such known processes and catalysts, it is believed that, in general, the production of methacrolein from isobutylene is more technically difficult than that of acrolein from propylene. In fact, it is known that when acrolein and methacrolein are produced respectively from propylene and isobutylene by using the same type of catalyst which is believed to be effective for catalytically converting olefins into corresponding unsaturated aliphatic aldehydes, the yield of methacrolein is usually lower than that of acrolein. For example, Japanese Patent Application Publication No. 47-42813(1972) states that the yield of methacrolein is 5 to 10% below that of acrolein. In this connection, it is presumed that the difference in yield between methacrolein and acrolein is derived from the fact that the methacrolein molecule has a branched carbon chain, that is, a methyl group, which is not contained in the acrolein molecule. Therefore, it is considered that, in order to convert isobutylene catalytically into methacrolein in a high yield, a new type of catalyst different from conventional catalysts effective for the catalytic oxidation of propylene into acrolein, should be provided.

The conventional catalysts for catalytically converting isobutylene into methacrolein usually contain as catalytic ingredients, molybdenum, bismuth, iron, cobalt and an alkali metal such as potassium (Mo-Bi-Fe-Co-K). This type of conventional catalysts is disclosed, for example, in Japanese Patent Application Publication No. 47-42813(1972) (Co-Fe-Bi-W-Mo-Si-K-P-O), Japanese Patent Application Publication No. 48-17253(1973) (Ni-Co-Fe-Bi-P-Cs-K-Mo-O), U.S. Pat. No. 3,966,823 (Ni-Co-Fe-Bi-P-K-Mo-O), U.S. Pat. No. 4,049,577 (Co-Fe-Bi-Mo-K-O), U.S.Pat. No. 3,825,502 (Co-Fe-Bi-Mg-K-Mo-O), Japanese Patent Application Publication No. 51-47684(1976) (Co-Fe-Bi-Cr-K-Mo-O), Japanese Patent Application Laying-open No. 48-52713(1973) (Co-Fe-Bi-Cs-K-Mo-O) and Japanese Patent Application Laying-open No. 51-34107(1976) (Mn-K-Ni-Co-Fe-Bi-Mo-O).

The above-mentioned types of conventional catalysts can enable methacrolein to be produced in a yield of approximately 70%. However, this level of yield is not high enough for industrial use.

Also, it was discovered by the inventors of the present invention that the conventional catalysts have relatively poor resistances to attrition and compression and also exhibit a relatively poor durability in resistances to attrition and compression. Therefore, the conventional catalysts are often disintegrated during the catalytic oxidizing operation. The disintegration of catalysts results in a reduction in the catalytic efficiency of the catalysts.

Under these circumstances, it is desired to provide a new type of catalyst which enables methacrolein to be produced in a high yield and which exhibits an enhanced mechanical strength and durability.

As a result of a study on the improvement of the catalyst, it was discovered by the inventors of the present invention that the catalytic efficiency and the mechanical strength and durability of the catalyst can be enhanced by using cesium as an alkali metal catalytic ingredient and by adding an additional catalytic ingredient consisting of at least one member selected from the group of vanadium and palladium, to the conventional catalytic ingredient, that is, molybdenum, bismuth, iron, cobalt and an alkali metal.

Furthermore, it was discovered by the inventors that the catalytic efficiency and the mechanical strength and durability of the above-mentioned catalyst can be further improved by adding an additional catalytic ingredient consisting of at least one member selected from titanium, nickel, tin and zirconium to the above-mentioned conventional additional catalytic ingredients.

The present invention is based on the above-mentioned discoveries.

SUMMARY OF THE INVENTION

An object of the present invention is to provide a process for producing methacrolein by the catalytic oxidation of isobutylene in a vapor phase with molecular oxygen at an elevated temperature in the presence of a catalyst which is capable of enhancing the yield of methacrolein and which has an enhanced mechanical strength and durability.

The above-mentioned object can be attained by the process of the present invention which comprises bringing a feed gas containing isobutylene and molecular oxygen into contact with a catalyst at a temperature of from 250° to 500° C., which process is characterized in that the catalyst is represented by the formula (1):

$$Mo_a Co_b Fe_c Bi_d Cs_e X_f Y_g O_h \tag{1}$$

wherein Mo represents a molybdenum atom, Co represents a cobalt atom, Fe represents an iron atom, Bi represents a bismuth atom, Cs represents a cesium atom, X represents at least one member selected from the group consisting of vanadium and palladium atoms, Y represents at least one member selected from the group consisting of titanium, nickel, tin and zirconium atoms, O represents an oxygen atom, the subscripts a through g respectively represent a positive number proportional to the number of respective metal atoms, wherein when a is 12, b through g fall respectively within the following ranges: b=2 to 12, c=0.5 to 7, d=0.1 to 5, e=0.0005 to 0.5, f=0.01 to 2 and g=0 to 5, and the subscript h represents a positive number proportional to the number of oxygen atoms satisfying the average valence of the above-mentioned metal atoms. It is preferable that the values of the subscripts b through g be respectively in the ranges of: b=4 to 10, c=1 to 5, d=0.5 to 4, e=0.01 to 0.3, f=0.05 to 1.5 and g=0.1 to 5.

DETAILED DESCRIPTION OF THE INVENTION

In the catalyst usable for the process of the present invention, it is important that cesium is used as an alkali metal catalytic ingredient, either or both of vanadium and palladium are added, as an additional catalytic ingredient, to the conventional catalytic ingredient, that is, molybdenum, bismuth, iron, cobalt and an alkali metal, and optionally, that a further additional catalytic ingredient consisting of one, two, or more members from the group consisting of titanium, nickel, tin and zirconium is added to the above-mentioned conventional and additional catalytic ingredients. If an alkali metal such as potassium, sodium, rubidium and lithium, which are different from cesium, is used, the resultant catalyst will cause methacrolein to be produced with a poor percent selectivity (which term will be defined hereinafter) and with a relatively low yield of 70% or less. Accordingly, the alkali metals which are different from cesium cannot be used to attain the object of the present invention. Evenif cesium is used as an alkali metal catalytic ingredient, if the additional catalytic ingredient consisting of at least one member selected from vanadium and palladium is not used, the resultant catalyst will cause methacrolein to be produced with a poor percent conversion of isobutylene (which term will be defined hereinafter), and also with a relatively low yield. Also, even if the additional catalytic ingredient is used, if cesium is not used as an alkali metal catalytic ingredient, the use of the resultant catalyst will result in a poor percent selectivity to methacrolein and in a relatively low yield of methacrolein.

In the conventional catalysts, it was believed that either the element phosphorus or arsenic is effective as an additional catalytic ingredient for enhancing the catalytic efficiency of the catalyst. However, surprisingly, in spite of the fact that neither the element phosphorus or arsenic is used, the use of a combination of cesium with the additional catalytic ingredient results not only in a high percent selectivity to methacrolein and a high yield of methacrolein, but also in a high mechanical strength, for example, resistance to attrition and crush strength, and durability of the resultant catalyst.

The addition of the further additional catalytic ingredient, consisting of at least one member selected from the group comprising titanium, nickel, tin and zirconium, is effective not only for enhancing the mechanical strength and durability of the resultant catalyst but also for increasing the yield of methacrolein.

The values of the subscripts a through h should be in the range as specified hereinbefore. If any value of a through h falls outside of the specified range, the resultant catalyst will cause the percent conversion of isobutylene and/or the percent selectivity to methacrolein to be poor.

In the process of the present invention, the use of the novel catalyst (as defined hereinafter) enhances both the percent conversion of isobutylene and the percent selectivity to methacrolein. Therefore, the yield of the resultant methacrolein can be increased by using the novel catalyst. Also, since the special catalyst usable for the present invention has an enhanced mechanical strength and durability, the process of the present invention can be uniformly carried out over a long period of time without disintegration of the catalyst and change in the catalytic efficiency of the catalyst. Accordingly, it is obvious that the process of the present invention can be very advantageous for continuously producing methacrolein on an industrial scale.

In the catalyst usable for the present invention, the respective metal ingredients are present in the form of metal oxides which include those of the type in which each single metal is bonded with oxygen, those of the type in which two or more metals are bonded with oxygen to form a complex and those of the type in which the above-mentioned two types of oxides are combined together.

The catalyst of the above formula (1), usable for the process of the present invention, may be prepared in any conventional manner by using, as the starting raw material, oxides, salts and other compounds, containing the above-mentioned metal ingredients. However, calcination of the catalyst, i.e., the final step of the catalyst preparation, should preferably be carried out at a temperature in the range of from 550° to 800° C., more preferably, from 580° to 750° C., and over a period of 1 to 20 hours, more preferably, from 2 to 10 hours, for obtaining the desired yield of methacrolein and catalyst strength. This temperature range is higher than the range of from 400° to 500° C. popularly employed for preparing the conventional catalysts based on molybdenum, bismuth, iron and cobalt.

A calcining temperature falling outside of the above-mentioned range may sometimes cause a decrease in the mechanical strength of the resultant catalyst and/or the yield of methacrolein. The calcining operation is carried out in a gas containing oxygen, usually an air atmosphere.

The general procedures for preparing a catalyst are as follows. Oxides, salts and other compounds containing the above-mentioned metal ingredients are mixed together in an aqueous medium to prepare a uniform slurry. The aqueous slurry is dried at a temperature not exceeding 300° C. In this case, the drying operation is preferably carried out in two steps. That is, in the first step, the aqueous dispersion is heated at a temperature of from 100° to 150° C., preferably at approximately 120° C., to evaporate water; and in the second step, the dried product is heated at a temperature of from 150° to 300° C. preferably at approximately 200° C., for a period of 3 to 20 hours to eliminate volatile substances, for example, ammonium nitrate and nitrogen oxides. The dried product is shaped into pellets or particles of a desired shape and size. The shaped pellets or particles are calcined under the above-mentioned conditions.

As examples of the starting raw materials which can be used in the preparation of the catalyst are, for example, molybdenum compounds such as molybdic acid, ammonium molybdate and molybdenum trioxide; cobalt compounds such as cobalt carbonate, cobalt nitrate, cobaltous oxide, tricobalt tetroxide, cobalt chloride, cobaltous hydroxide, cobaltic hydroxide and cobalt sulfide; iron compounds such as ferrous nitrate, ferric nitrate, ferrous oxide, ferric oxide, ferrous carbonate, ferrous sulfide, ferrous chloride, ferric chloride, ferrous hydroxide, ferric hydroxide, ferrous sulfate, ferric sulfate, ammonium ferrous sulfate and ammonium ferric sulfate; bismuth compounds such as bismuth nitrate, bismuth dichloride, bismuth trichloride, bismuth pentoxide, bismuth trioxide, bismuth tetroxide, bismuth oxynitrate, bismuth hydroxide, bismuth subnitrate and bismuth oxychloride; cesium compounds such as cesium nitrate, cesium chloride, cesium hydroxide, cesium carbonate and cesium oxide; vanadium compounds such as vanadium chloride, ammonium metavanadate, vanadyl chloride, vanadyl sulfate and vanadium pentoxide; palladium compounds such as palladium nitrate, palladium hydroxide, palladium chloride and palladium oxide; titanium compounds such as titanium dioxide, titanic acid, titanium trichloride and titanium tetrachloride; nickel compounds such as nickel carbonates, nickel nitrate, nickel oxide, dinickel trioxide, nickel chloride, nickel hydroxide and nickel sulfate; tin compounds such as stannic oxide, tin hydroxide, stannic chloride, stannous oxide and stannic acid; and zirconium compounds such as zirconium oxide, zirconium oxynitrate and zirconium hydroxide. Among the above-mentioned compounds, the compounds which are most preferable as starting raw materials are nitrates and ammonium salts of the respective ingredient metals.

The procedures for preparing a catalyst usable for the present invention will be described in more detail with reference to a catalyst consisting of molybdenum, bismuth, iron, cobalt, cesium, vanadium and oxygen.

Predetermined amounts of ammonium molybdate and ammonium metavanadate are dissolved in water, preferably warm water, to prepare an aqueous solution. Added by drops to this aqueous solution, while the solution is being stirred, are an acidic solution of a predetermined amount of bismuth nitrate in nitric acid and an aqueous solution of predetermined amounts of ferric nitrate, cobalt nitrate and cesium nitrate. The so-obtained aqueous slurry is then heated at a temperature of from 100° to 150° C., preferably at approximately 120° C., by using a drum dryer or a spray dryer to evaporate water from the slurry. Next, the slurry is again heated at a temperature of from 150° to 300° C., preferably at approximately 200° C., until no more ammonium nitrate and nitrogen oxides are evolved from the dried product and the slurry is completely dried. The resultant dried product is shaped or granulated into a desired shape and size of pellets or particles. If necessary, the particles can be separated by using a screen having a desired mesh to collect particles having a particular desired size. The particles are finally calcined, preferably at a temperature of from 550° to 800° C., more preferably, from 580° to 750° C.

In the case where palladium is used in place of vanadium as a catalytic metal ingredient, it is preferable to use palladium nitrate as a starting raw material. A predetermined amount of palladium nitrate is dissolved together with ferric nitrate, cobalt nitrate and cesium nitrate in warm water. The solution is added dropwise into a solution of ammonium molybdate alone in warm water while the resultant mixture is being stirred.

In the case where titanium is added as a catalytic metal ingredient, it is preferable that titanium dioxide be suspended in an aqueous solution of ammonium molybdate alone or together with ammonium metavanadate. Also, in the case where the catalyst contains a further additional catalytic ingredient, it is preferable to carry out the calcining operation at a temperature of from 550° to 800° C., more preferably, from 580° to 750° C., in order to increase the reproducibility in the catalytic activity and the durability of the catalyst.

The catalyst may be used alone or in combination with a carrier. Carriers such as those known for supporting conventional oxidation catalysts and for bringing about favorable effects to the reaction involved, e.g., silica, alumina, silica-alumina, titania, diatomaceous earth and carborundum, may be used. These carriers may be combined with the catalyst either during or after preparation of the catalyst.

In general, the size and shape of the catalyst particle used, and the use of a carrier are not critical factors because they do not greatly affect the resultant catalytic activity.

In carrying out the process of the present invention, it is not necessary to use a highly purified isobutylene. Thus, the isobutylene may contain other hydrocarbons, for example, n-butane and n-butene. That is, the source of isobutylene may be a $C_4$ fraction which is produced from naphtha cracking and which contains, as main components, isobutylene n-butene, 1,3-butadiene and n-butane. Another source of isobutylene may be a hydrocarbon mixture which is a residue obtained by extracting 1,3-butadiene from the $C_4$ fraction. This hydrocarbon mixture contains isobutylene and n-butene predominantly. When this type of hydrocarbon mixture is used as a source of isobutylene for the process of the present invention, not only isobutylene is converted into methacrolein but n-butene is also converted into 1,3-butadiene. That is, in this case, methacrolein and 1,3-butadiene, which are both useful for industrial uses, are simultaneously produced, thus constituting an advantage from an economic view point. The hydrocarbon mixture may contain isobutane, n-butane and propane, in addition to isobutylene and n-butene. In this case, it is preferable for the sum of the molar amounts of isobutylene and n-butene to correspond to 50% or more, more preferably, to 70% or more, with respect to the total molar amount of the hydrocarbon mixture.

In carrying out the process of the present invention, an inert gas which is not reactive to catalytic oxidation may be used as a diluent gas for the feed gas. The diluent gas may be steam, nitrogen gas, carbon dioxide gas, n-butane gas, isobutane gas or propane gas.

Likewise, the molecular oxygen used also needs not be highly purified. That is, oxygen-containing gases, such as air or a mixture of pure molecular oxygen and the above-mentioned diluent gas, may be conveniently used. Air particularly, may be advantageously used. The relative proportion of molecular oxygen in the feed gas is usually in the range of from 0.4 to 5 moles, more preferably, from 0.5 to 3 moles, per mole of isobutylene.

The catalytic oxidation of the present invention is carried out at a temperature in the range of from 250° to 500° C., preferably from 300° to 480° C. The contact time is usually in the range of from 0.2 to 20 seconds, preferably from 0.5 to 15 seconds.

The reaction may be carried out under atmospheric pressure although superatmospheric or subatmospheric pressure may be used if desired.

The catalytic oxidation reaction may be carried out in a fixed bed, a moving bed or a fluidized bed. When a fluidized bed is employed, it is preferable to use a catalyst having a particle size in the range of from 30 to 100 microns.

If it is necessary, the resultant methacrolein can be isolated from the reaction mixture by using any kind of conventional isolating processes, for example, by the absorption of methacrolein by cold water followed by the stripping and distillation of methacrolein.

The present invention will be further clarified by the Examples and Comparison Examples set forth below. In all of the examples, "%" is expressed by weight unless otherwise specified. In these examples, the selective conversion of isobutylene to methacrolein and yield of methacrolein were calculated in accordance with the following equations.

Percent conversion of isobutylene =
$$\frac{\text{moles of isobutylene consumed}}{\text{moles of isobutylene fed}} \times 100$$

Percent selectivity to methacrolein =
$$\frac{\text{moles of methacrolein produced}}{\text{moles of isobutylene consumed}} \times 100$$

Percent yield of methacrolein =
$$\frac{\text{moles of methacrolein produced}}{\text{moles of isobutylene fed}} \times 100$$

The moles of isobutylene fed, the moles of isobutylene consumed and the moles of methacrolein produced were determined after one hour had elapsed from the start of the reaction.

The crush strength of the catalyst was determined as follows.

A catalyst tablet (5 mm in diameter and 5 mm in height) was placed on a testing plate and compressed by using a Kiya-type hardness tester until the tablet was crushed. The value of the compressive load in Kg under which the tablet was crushed was measured. The above-mentioned testing procedures were repeated 50 times. The crush strength of the catalyst tablet was represented by an average value calculated from the results of 50 tests.

The resistance of the catalyst to attrition was determined as follows.

A glass test tube having an inner diameter of 2.54 cm and a height of 300 cm was used. 50 tablets of a catalyst were dropped down from the top of the glass test tube to the bottom thereof. The total weight of the tablets which were crushed into particules having 6 mesh size or less was measured. The resistance of the catalyst to attrition was thereafter represented by a ratio (%) of the weight of the crushed tablets to the weight of the original 50 tablets.

EXAMPLE 1

141.3 g of ammonium molybdate [$(NH_4)_6Mo_7O_{24} \cdot 4H_2O$] and 0.78 g of ammonium metavanadate [$NH_4VO_3$] were dissolved in 200 ml of water maintained at a temperature of 40° C. A solution of 38.8 g of bismuth nitrate [$Bi(NO_3)_3 \cdot 5H_2O$] in 50 ml of a 15% nitric acid aqueous solution was mixed into a solution of 64.6 g of ferric nitrate [$Fe(NO_3)_3 \cdot 9H_2O$], 0.078 g of cesium nitrate [$CsNO_3$] and 186.2 g of cobalt nitrate [$Co(NO_3)_2 \cdot 6H_2O$] in 200 ml of water of a temperature adjusted to 40° C. The mixture was admixed dropwise into the above-prepared aqueous solution of ammonium molybdate and ammonium metavanadate while the admixed solution was being stirred.

The admixed solution was first dried at a temperature of 120° C. by using a drum dryer. The initially dried material was additionally dried at a temperature of 200° C. for 10 hours by using an oven. The resultant material was shaped into tablets having a diameter of 5 mm and a height of 5 mm by means of a tablet-forming machine. The tablets were calcined at a temperature of 650° C. for 5 hours in an air atmosphere to provide a catalyst. In the catalyst thus prepared, the atomic ratio of Mo:Bi:Co:Fe:Cs:V was 12:1:8:2:0.005:0.1.

10 ml of the catalyst tablets were charged into a U-shaped glass tube having an inner diameter of 8 mm. A feed gas containing isobutylene, air and steam in a molar ratio of 1:10:6 was passed through the U-shaped tube at a temperature of 390° C. at a flow rate of 180 ml/min so that the contact time of the feed gas with the catalyst tablets was 3.3 seconds. The percent conversion of isobutylene, the percent selectivity to methacrolein and the yield of methacrolein were determined. The results of Example 1 are shown in Table 1.

EXAMPLES 2 THROUGH 6

In each of Examples 2 through 6, the same procedures as those described in Example 1 were carried out, except that the atomic ratio of Mo:Bi:C0:Fe:Cs:V was varied for each of the Examples 2 through 6 in accordance with the ratios shown in Table 1. In example 3, the catalytic oxidation was carried out at a temperature of 380° C. The results of Examples 2 through 6 are shown in Table 1.

EXAMPLES 7 AND 8

In each of Examples 7 and 8, procedures identical to those described in Example 1 were carried out, except that 1.84 g of palladium nitrate [$Pd(NO_3)_2$] were added to the mixed solution. The atomic ratio of Mo:Bi:Co:Fe:Cs:V:Pd for each of Examples 7 and 8 is respectively shown in Table 1. Also, in Example 7, the catalytic oxidation was carried out at a temperature of 380° C. The results of Examples 7 and 8 are shown in Table 1.

EXAMPLES 9 AND 10

In each of Examples 9 and 10, the same procedures as those used in Example 8 were carried out, except that no ammonium metavanadate was used. The atomic ratio of Mo:Bi:Co:Fe:Cs:Pd for each of the two examples is respectively shown in Table 1. In Example 9, the catalytic contacting temperature was 360° C. The results of Examples 9 and 10 are shown in Table 1.

Table 1

| Example No. | Composition of Catalyst (Atomic ratio) | | | | | | | Catalytic contacting temperature (°C.) | Conversion of isobutylene (%) | Selectivity to methacrolein (%) | Yield of methacrolein (%) |
|---|---|---|---|---|---|---|---|---|---|---|---|
| | Mo | Co | Fe | Bi | Cs | V | Pd | | | | |
| 1 | 12 | 8 | 2 | 1 | 0.005 | 0.1 | — | 390 | 96.5 | 87.2 | 84.1 |
| 2 | 10 | 8 | 2 | 1 | 0.05 | 0.1 | — | 390 | 95.3 | 86.4 | 82.3 |
| 3 | 10 | 8 | 2 | 1 | 0.1 | 0.5 | — | 380 | 94.9 | 86.0 | 81.6 |
| 4 | 12 | 7 | 4 | 1 | 0.01 | 0.1 | — | 390 | 94.8 | 86.9 | 82.4 |
| 5 | 12 | 8 | 3 | 2 | 0.01 | 0.1 | — | 390 | 98.9 | 84.7 | 83.8 |
| 6 | 11 | 6 | 4 | 1 | 0.01 | 0.1 | — | 390 | 96.9 | 85.9 | 83.2 |
| 7 | 10 | 8 | 2 | 1 | 0.05 | 0.1 | 0.1 | 380 | 98.3 | 84.5 | 83.1 |
| 8 | 11 | 8 | 3 | 1 | 0.01 | 0.1 | 0.1 | 390 | 97.3 | 85.0 | 82.7 |
| 9 | 10 | 8 | 2 | 1 | 0.005 | — | 0.1 | 360 | 97.8 | 84.3 | 82.4 |
| 10 | 10 | 8 | 2 | 1 | 0.1 | — | 0.5 | 390 | 96.8 | 85.7 | 83.0 |

(Contact time: 3.3 seconds)

COMPARISON EXAMPLE 1

The same procedures as those described in Example 1 were carried out, except that neither cesium nitrate nor ammonium metavanadate were used, the atomic ratio of the metal ingredients was the same as that shown in Table 2 and the catalytic contacting temperature was 370°C. The results of Comparative Example 1 are shown in Table 2.

COMPARISON EXAMPLES 2 AND 3

In each of Examples 2 and 3, the same procedures as those described in Example 1 were carried out, except that no ammonium metavanadate was used and the atomic ratio of the metal ingredients in the catalyst for each of the two comparison Examples was the same as that respectively shown in Table 2. The results of Comparison Examples 2 and 3 are shown in Table 2.

COMPARISON EXAMPLES 4 THROUGH 7

In each of Examples 4 through 7, the same procedures as those described in Example 1 were carried out, except that no ammonium metavanadate was used, cesium nitrate which served as the raw material for the alkali metal catalytic ingredient was replaced respectively by sodium nitrate in Comparison Example 4, by rubidium nitrate in Comparison Example 5 and by potassium nitrate in Comparison Examples 6 and 7 in accordance with the amounts respectively shown in Table 2, and the atomic ratio of the metal ingredients in the resultant catalyst for each of these Comparison Examples was the same as that respectively shown in Table 2. In Comparison Examples 4 and 7, catalytic oxidation was carried out at a temperature of 370° C. The results of Comparison Examples 4 through 7 are shown in Table 2.

COMPARISON EXAMPLE 8

The same procedures as those described in Example 1 were carried out, except that no cesium nitrate was used, the atomic ratio of the metal ingredients in the resultant catalyst was the same as that shown for this Comparison Example in Table 2, and catalytic oxidation was carried out at a temperature for a contact time as specified in Table 2 for this Comparison Example. The results of Comparison Example 8 are shown in Table 2.

COMPARISON EXAMPLE 9

A comparison catalyst having an atomic ratio of the catalytic metal ingredients as shown in Table 2 was prepared by following procedures similar to those used in Example 9, except that no cesium nitrate was used. The same reaction procedures as those described in Example 1 were carried out, except that the contacting temperature and the contact time followed were those shown in Table 2 for this Comparison Example 9. The results of Comparison Example 9 are shown in Table 2.

COMPARISON EXAMPLES 10 THROUGH 12

In each of Comparison Examples 10 through 12, a comparison catalyst was prepared by following the same procedures as those described in Example 1, except that cesium nitrate which served as a raw material of alkali metal catalytic ingredient was replaced respectively by potassium nitrate in Comparison Example 10, by sodium nitrate in Comparison Example 11 and by rubidium nitrate in Comparison Example 12. Also, a catalytic conversion of isobutylene was carried out by carrying out the same procedures as those described in Example 1, except that the above-prepared comparison catalyst was used, and the contacting temperature and the contact time followed were those respectively specified in Table 2 for Comparison Examples 10 through 12.

The comparison catalysts of Comparison Examples 11 and 12 were prepared by calcining at temperatures of 660° C. and 620° C., respectively.

The results of both Comparison Examples are shown in Table 2.

Table 2

| Comparison Example No. | Composition of catalyst (Atomic ratio) | | | | | | | Contact time (sec) | Catalytic contacting temperature (°C.) | Conversion of isobutylene (%) | Selectivity to methacrolein (%) | Yield of methacrolein (%) |
|---|---|---|---|---|---|---|---|---|---|---|---|---|
| | Mo | Co | Fe | Bi | Alkali metal | V | Pd | | | | | |
| 1 | 10 | 8 | 2 | 1 | — | — | — | 3.3 | 370 | 96.2 | 50.5 | 48.5 |
| 2 | 10 | 8 | 2 | 1 | Cs = 0.03 | — | — | 3.3 | 390 | 74.9 | 84.3 | 63.1 |
| 3 | 10 | 8 | 2 | 1 | Cs = 0.1 | — | — | 3.3 | 390 | 25.2 | 87.0 | 21.9 |
| 4 | 10 | 8 | 3 | 1 | Na = 0.5 | — | — | 3.3 | 370 | 97.3 | 68.2 | 66.4 |
| 5 | 10 | 8 | 3 | 1 | Rb = 0.05 | — | — | 3.3 | 390 | 94.1 | 70.5 | 66.3 |
| 6 | 10 | 8 | 2 | 1 | K = 0.01 | — | — | 3.3 | 370 | 96.8 | 69.3 | 67.1 |
| 7 | 10 | 8 | 2 | 1 | K = 0.3 | — | — | 3.3 | 390 | 91.0 | 72.3 | 65.8 |
| 8 | 10 | 8 | 2 | 1 | — | 0.1 | — | 3.0 | 360 | 98.3 | 64.1 | 63.0 |
| 9 | 10 | 8 | 2 | 1 | — | — | 0.1 | 3.0 | 340 | 95.0 | 58.2 | 55.3 |
| 10 | 10 | 8 | 2 | 1 | K = 0.05 | 0.1 | — | 3.0 | 370 | 97.6 | 68.2 | 66.6 |
| 11 | 10 | 8 | 2 | 1 | Na = 0.1 | 0.1 | — | 3.0 | 370 | 95.2 | 65.4 | 62.3 |
| 12 | 10 | 8 | 2 | 1 | Rb = 0.1 | 0.1 | — | 3.0 | 390 | 89.3 | 75.1 | 67.1 |

COMPARISON EXAMPLES 13 THROUGH 17

In each of Comparison Examples 13 through 17, a comparison catalyst was prepared by following the same procedures as those described in Example 1, except that the amounts of the raw materials of respective catalytic metal ingredients used were changed so that the resultant comparison catalysts had a catalytic metal ingredient composition, as shown in Table 3, which is outside of the scope of the present invention.

In addition, the calcining temperature was adjusted to 600° C. in Comparison Examples 13 and 14, to 650° C. in Comparison Example 15, to 570° C. in Comparison Example 16 and to 660° C. in Comparison Example 17.

By using the comparison catalysts, the same procedures for converting isobutylene as those described in Example 1 were carried out, except that the contacting temperature and the contact time were changed to those shown respectively in Table 3 for Comparison Examples 13 through 17.

The results are shown in Table 3.

COMPARISON EXAMPLE 18

A comparison catalyst was prepared in accordance with the same procedures as those used in Example 9, except that the cesium nitrate as a raw material of an alkali metal catalytic ingredient was replaced by potassium nitrate and the resultant catalyst had the composition described in Table 3. Next, the same procedures for catalytically converting isobutylene as those described in Example 1 were carried out, except that the contacting temperature and the contact time were changed to those shown in Table 3 for Comparison Example 18.

The results for this Comparison Example are shown in Table 3.

COMPARISON EXAMPLE 19

A comparison catalyst was prepared by following the same procedures as those used in Example 9, except that the amount of palladium nitrate employed was changed to a value which caused the composition of the resultant catalyst to be changed to that shown in Table 3 for Comparison Example 19, and the calcining temperature of 650° C. was changed to 670° C. The resultant catalyst was used for carrying out the same procedures as those mentioned in Example 1 for catalytically converting isobutylene, except that the contacting temperature and the contact time were changed to those shown in Table 3 for Comparative Example 19.

The results for this Comparative Example are shown in Table 3.

From a comparison of the results of Examples 1 through 10 shown in Table 1 with those of Comparison Examples 1 through 19 shown in Tables 2 and 3, it is clear that the process of the present invention produced a high percent yield of methacrolein, because the percent conversion of isobutylene and the percent selectivity to methacrolein of this process were both at a high level. On the contrary, the processes of Comparison Examples 1 through 19 produced a relatively low percent yield of methacrolein, because either or both of the percent conversion of isobutylene and percent selectivity to methacrolein of these processes were at a low level.

tained at a substantially constant level during the entire reaction.

The crush strength the catalyst tablets was 5.1 Kg 1 hour after the start of the reaction and 5.1 Kg 100 hours after the start of the reaction. That is, it was confirmed that the crush strength of the catalyst tablets did not change at all even though the tablets were continuously used for a long period of time.

EXAMPLE 12

By using the same catalyst ($Mo_{10}Co_8Fe_2Bi_1Cs_{0.1}Pd_{0.5}$) as that mentioned in Example 10, the same contacting procedures as those described in Example 1 were continuously carried out for 100 hours. After 100 hours had elapsed from the start of carrying out the contacting procedures, the percent conversion of isobutylene, the percent selectivity to methacrolein and the percent yield of methacrolein were respectively 96.5%, 85.8% and 82.8% which were similar to those observed 1 hour after the start of carrying out the contacting procedures.

It was also confirmed that the crush strength of the catalyst tablets could be maintained constant during the contacting process. That is, 100 hours after the start of the process, the crush strength was observed to be 5.3 Kg, the same crush strength as that observed after 1 hour from the start of the process.

EXAMPLE 13

The same procedures as those described in Example 1 were carried out and the catalyst tablets ($Mo_{12}Bi_1Co_8Fe_2Cs_{0.005}V_{0.1}$) were accordingly charged into a U-shaped reaction tube. A feed gas, containing 10 parts by volume of a hydrocarbon mixture gas, 100 parts by volume of air and 60 parts by volume of steam, was passed through the reaction tube at a flow rate of 170 ml/min under such a condition that the contact of the feed gas with the catalyst was maintained for 3.3 seconds at a temperature of 390° C.

A hydrocarbon gas mixture was a residual gas of the process in which 1,3-butadiene was extracted from a $C_4$ fraction produced during the process of naphtha cracking. This hydrocarbon gas mixture had a composition as Table 3

| Comparison Example No. | Composition of catalyst (Atomic ratio) | | | | | | | Contact time (sec) | Catalytic contacting temperature (°C.) | Conversion of isobutylene (%) | Selectivity to methacrolein (%) | Yield of methacrolein (%) |
|---|---|---|---|---|---|---|---|---|---|---|---|---|
| | Mo | Co | Fe | Bi | Alkali metal | V | Pd | | | | | |
| 13 | 12 | 1 | 6 | 1 | Cs = 0.01 | 0.1 | — | 3.3 | 390 | 93.7 | 69.3 | 64.9 |
| 14 | 13 | 8 | 0.5 | 1 | Cs = 0.01 | 0.1 | — | 3.3 | 390 | 95.4 | 67.8 | 64.7 |
| 15 | 12 | 8 | 3 | 0.05 | Cs = 0.01 | 0.1 | — | 3.0 | 390 | 90.4 | 73.8 | 66.7 |
| 16 | 11 | 8 | 2 | 1 | Cs = 0.75 | 0.1 | — | 3.3 | 410 | 32.9 | 86.4 | 28.4 |
| 17 | 12 | 8 | 3 | 1 | Cs = 0.01 | 3 | — | 3.0 | 370 | 98.1 | 55.7 | 54.6 |
| 18 | 10 | 8 | 2 | 1 | K = 0.05 | — | 0.1 | 3.0 | 370 | 99.3 | 60.4 | 60.0 |
| 19 | 12 | 8 | 3 | 1 | Cs = 0.01 | — | 3 | 3.0 | 360 | 97.3 | 52.1 | 50.7 |

EXAMPLE 11

The same procedures for catalytically converting isobutylene into methacrolein as those described in Example 1 were continuously carried out for 100 hours by using the same catalyst ($Mo_{12}Co_8Fe_2Bi_1Cs_{0.005}V_{0.1}$) as that mentioned in Example 1.

After 100 hours had elapsed from the start of the reaction, the percent conversion of isobutylene was 93.8%, the percent selectivity to methacrolein was 87.5% and the percent yield of methacrolein was 82.1%. That is, the yield of methacrolein was main-that shown in Table 4 for example 13.

Table 4

| Compound | Molar percent |
|---|---|
| Propane | 0.1 |
| Propylene | 0.5 |
| Isobutane | 1.5 |
| n-Butane | 8.1 |
| n-Butene | 41.9 |
| Isobutylene | 47.0 |
| 1,3-Butadiene | 0.4 |

Table 4-continued

| Compound | Molar percent |
|---|---|
| Propadiene | 0.5 |

The results of Example 13 are shown in Table 5.

Table 5

| Item | Percent |
|---|---|
| Conversion of isobutylene | 97.2 |
| Selectivity to methacrolein | 84.2 |
| Yield of Methacrolein | 81.6 |
| Conversion of n-butene(*) | |
| Selectivity to 1,3-butadiene(**) | 75.4 |

Note:
(*)Percent conversion of n-butene
$= \frac{\text{moles of n-butene consumed}}{\text{moles of n-butene fed}} \times 100$
(**)Percent selectivity to 1,3-butadiene
$= \frac{\text{moles of 1,3-butadiene produced}}{\text{moles of n-butene consumed}} \times 100$

EXAMPLE 14

In 200 ml of warm water maintained at a temperature of 40° C., 141.3 g of ammonium molybdate [(NH$_4$)$_6$Mo$_7$O$_{24}$.4H$_2$O] and 0.78 g of ammonium metavanadate [NH$_4$VO$_3$] were dissolved and 6.39 g of titanium dioxide were suspended. A mixture of a solution of 38.8 g of bismuth nitrate [Bi(No$_3$)$_3$.5H$_2$O] in 50 ml of a 15% nitric acid aqueous solution and a solution of 64.6 g of ferric nitrate [Fe(NO$_3$)$_3$.9H$_2$O], 0.078 g of cesium nitrate [CsNO$_3$] and 186.2 g of cobalt nitrate [Co(NO$_3$)$_2$.6H$_2$O] in 200 ml of warm water maintained at a temperature of 40° C., was admixed dropwise into the thus-prepared aqueous solution suspension while the admixed solution was being stirred.

The admixed aqueous slurry was initially dried at a temperature of 120° C. by using a drum dryer, and then the first dried product was dried for a second time at a temperature of 200° C. for 10 hours by using an oven. The second dried product was shaped into tablets each having a diameter of 5 mm and a height of 5 mm by using a tablet-forming machine. The resultant tablets were calcined in an air atmosphere at a temperature of 650° C. for 5 hours. The resultant catalyst had an atomic ratio of Mo:Bi:Co:Fe:Cs:V:Ti=12:1:8:2:0.005:0.1:1. The measured crush strength and resistance to attrition of the catalyst tablets are shown in Table 6. 10 ml of the catalyst tablets were placed in a U-shaped glass reaction tube having an inner diameter of 8 mm. A feed gas consisting of isobutylene, air and steam in a molar ratio of 1:10:6 was passed through the reaction tube at a flow rate of 200 ml/min under such a condition that the contact of the feed gas with the catalyst was maintained for 3.0 seconds at a temperature of 390° C.

The results of Example 14 are shown in Table 6.

EXAMPLES 15 THROUGH 19

The same procedures as those described in Example 14 were carried out, except that the titanium dioxide was replaced by zirconium oxide in Example 15, by stannic oxide in Example 16, by nickel oxide in Example 17, by a mixture of zirconium oxide and stannic oxide in Example 18 and by a mixture of titanium dioxide and stannic oxide in Example 19 respectively in the amounts shown in Table 6, and that, in only Example 16, the conversion of isobutylene was carried out at a temperature of 370° C. The obtained catalysts had the compositional make-ups, crush strength the resistance to attrition as shown in Table 6.

The results of the conversion of isobutylene in the respective Examples 15 through 18 are shown in Table 6.

EXAMPLE 20

Procedures identical to those described in Example 14 were carried out, except that no ammonium metavanadate was used and palladium nitrate was contained in the aqueous solution of ferric nitrate, cesium nitrate and cobalt nitrate. The resultant catalyst tablets has the compositional make-ups crush strength and the resistance to attrition as shown in Table 6.

Also, the results of the catalytic conversion of isobutylene are shown in Table 6.

EXAMPLES 21, 22 AND 23

Procedures identical to those used in Example 20 were conducted, except that the titanium dioxide employed in Example 20 was replaced by zirconium oxide in Example 21, by stannic oxide in Example 22, and by nickel oxide in Example 23 and that the resultant catalyst had the compositional make-ups, crush strength and resistance to attrition as shown in Table 6. Also, the results of the catalytic conversion of isobutylene are shown in Table 6.

EXAMPLES 24 AND 25

Procedures identical to those described in Example 14 were carried out, except that in both Examples 24 and 25, palladium nitrate was added to the aqueous solution of ferric nitrate, cesium nitrate and cobalt nitrate and the conversion of isobutylene was conducted at a temperature of 370° C. In Example 25, the titanium dioxide was replaced by stannic oxide. The catalyst tablets prepared had the compositional make-ups crush strength and the resistance to attrition as shown in Table 6.

The results of the conversions of isobutylene in both Examples 24 and 25 are also shown in Table 6.

EXAMPLE 26

Procedures identical to those used in Example 15 were carried out, except that no zirconium nitrate was employed.

The results of Example 26 are shown in Table 6.

EXAMPLE 27

Procedures identical to those used in Example 25 were conducted, except that neither ammonium metavanadate nor stannic oxide were employed.

The results of Example 27 are shown in Table 6.

Table 6

| Example No. | Composition of catalyst (Atomic ratio) | | | | | | | Crush strength (kg/tablet) | Resistance to attrition (% by weight) | Conversion of isobutylene (%) | Selectivity to methacrolein (%) | Yield of metharcrolein (%) |
|---|---|---|---|---|---|---|---|---|---|---|---|---|
| | Mo | Co | Fe | Bi | Cs | X | Y | | | | | |
| 14 | 12 | 8 | 2 | 1 | 0.005 | V = 0.1 | Ti = 1 | 6.5 | 0.03 | 95.3 | 89.9 | 85.7 |
| 15 | 10 | 8 | 2 | 1 | 0.01 | V = 0.1 | Zr = 1 | 6.8 | 0.02 | 94.9 | 89.0 | 84.5 |
| 16 | 10 | 8 | 3 | 1 | 0.005 | V = 0.2 | Sn = 2 | 6.2 | 0.04 | 97.3 | 87.0 | 84.7 |

Table 6-continued

| Example No. | Composition of catalyst (Atomic ratio) | | | | | | | Crush strength (kg/tablet) | Resistance to attrition (% by weight) | Conversion of isobutylene (%) | Selectivity to methacrolein (%) | Yield of methacrolein (%) |
|---|---|---|---|---|---|---|---|---|---|---|---|---|
| | Mo | Co | Fe | Bi | Cs | X | Y | | | | | |
| 17 | 10 | 8 | 3 | 1 | 0.01 | V = 0.1 | Ni = 1 | 6.6 | 0.03 | 97.0 | 87.4 | 84.8 |
| 18 | 10 | 8 | 2 | 1 | 0.01 | V = 0.1 | Zr = 1, Sn = 1, Ti = 1 | 6.4 | 0.02 | 98.9 | 86.3 | 85.4 |
| 19 | 10 | 8 | 2 | 1 | 0.01 | V = 0.2 | Sn = 1 | 6.8 | 0.02 | 95.9 | 87.1 | 83.5 |
| 20 | 10 | 8 | 2 | 2 | 0.05 | Pd = 0.1 | Ti = 1 | 7.3 | 0.02 | 94.3 | 89.1 | 84.0 |
| 21 | 10 | 8 | 3 | 2 | 0.01 | Pd = 0.2 | Zr = 2 | 6.4 | 0.05 | 97.6 | 87.2 | 85.1 |
| 22 | 10 | 8 | 2 | 1 | 0.01 | Pd = 0.1 | Sn = 2 | 7.1 | 0.01 | 96.8 | 87.0 | 84.2 |
| 23 | 10 | 7 | 3 | 0.5 | 0.01 | Pd = 0.1, V = 0.1 | Ni = 2 | 6.0 | 0.06 | 95.3 | 88.2 | 84.0 |
| 24 | 10 | 8 | 2 | 1 | 0.01 | Pd = 0.1, V = 0.1 | Ti = 1 | 5.9 | 0.03 | 98.1 | 86.0 | 84.4 |
| 25 | 10 | 8 | 2 | 0.5 | 0.01 | Pd = 0.1 | Sn = 2 | 7.3 | 0.04 | 96.5 | 88.8 | 85.7 |
| 26 | 10 | 8 | 2 | 1 | 0.01 | V = 0.1 | 0 | 5.0 | 0.25 | 92.8 | 86.7 | 80.5 |
| 27 | 10 | 8 | 2 | 0.5 | 0.01 | Pd = 0.1 | 0 | 5.3 | 0.31 | 95.8 | 84.4 | 80.9 |

From a comparison of the results of Examples 14 through 25 with those of Examples 26 and 27, it is clear that the use of a further additional catalytic ingredient consisting of at least one member selected from titanium, tin and zirconium causes the crush strength and the resistance to attrition of the catalyst tablets to be enhanced and the yield of methacrolein to be increased.

COMPARISON EXAMPLES 20 THROUGH 27

In each of Comparison Examples 20 through 27, the same procedures as those described in Example 14 were carried out, except that the preparation of the catalyst was effected in such a manner that the resultant catalyst had a composition, as shown in Table 7, which composition is outside of the scope of the present invention. In each of Comparison Examples 21 and 27, the contact of the feed gas with the catalyst was carried out at a temperature of 370° C.

The results of Comparison Examples 20 through 27 are shown in Table 7.

Table 7

| Comparison Example No. | Composition of catalyst (Atomic ratio) | | | | | | | Conversion of isobutylene (%) | Selectivity to methacrolein (%) | Yield of methacrolein (%) |
|---|---|---|---|---|---|---|---|---|---|---|
| | Mo | Co | Fe | Bi | Alkali metal | X | Y | | | |
| 20 | 10 | 8 | 3 | 1 | 0 | 0 | Ti = 2 | 86.5 | 68.2 | 59.0 |
| 21 | 10 | 8 | 2 | 1 | 0 | V = 0.5 | Sn = 1 | 92.6 | 73.1 | 67.7 |
| 22 | 10 | 8 | 3 | 1 | 0 | Pd = 0.1 | Zr = 1 | 95.2 | 69.8 | 66.4 |
| 23 | 10 | 8 | 2 | 1 | 0 | Pd = 0.1 | Ni = 1 | 93.8 | 65.7 | 61.6 |
| 24 | 10 | 8 | 2 | 2 | 0 | 0 | Zr = 3 | 91.3 | 74.1 | 67.7 |
| 25 | 10 | 8 | 2 | 2 | Cs = 0.01 | V = 0.1 | Ti = 7 | 68.4 | 89.3 | 61.1 |
| 26 | 10 | 8 | 2 | 1 | Cs = 0.005 | 0 | Ti = 1 | 90.3 | 85.1 | 76.8 |
| 27 | 10 | 8 | 2 | 1 | K = 0.05 | V = 0.1 | 0 | 97.4 | 68.1 | 66.3 |

What we claim is:

1. A process for producing methacrolein by the catalytic oxidation of isobutylene, comprising bringing a feed gas containing isobutylene and molecular oxygen into contact with a catalyst at a temperature of from 250° to 500° C., which process is characterized in that said catalyst is represented by the formula (1):

$$Mo_a Co_b Fe_c Bi_d Cs_e X_f Y_g O_h \quad (1)$$

wherein Mo represents a molybdenum atom, Co represents a cobalt atom, Fe represents an iron atom, Bi represents a bismuth atom, Cs represents a cesium atom, X represents at least one member selected from the group consisting of vanadium and palladium atoms, Y represents at least one member selected from the group consisting of titanium, nickel, tin and zirconium atoms, O represents an oxygen atom, the subscripts a through g respectively represent a positive number proportional to the number of respective metal atoms, wherein when a=12, b through g fall respectively within the following ranges: b=2 to 12, c=0.5 to 7, d=0.1 to 5, e=0.005 to 0.5, f=0.01 to 2 and g=0 to 5, and the subscript h represents a positive number proportional to the number of oxygen atoms satisfying the average valency of respective metal atoms.

2. A process as claimed in claim 1, wherein said contacting temperature is in a range of from 300° to 480° C.

3. A process as claimed in any one of claims 1 and 2, wherein the contact time is in a range of from 0.2 to 20 seconds.

4. A process as claimed in any one of claims 1 or 2, wherein said catalyst is combined with a carrier consisting of at least one member selected from the group consisting of silica, alumina, alumina-silica, titania, diatomaceous earth and carborundum.

5. A process as claimed in any one of claims 1 or 2, wherein said feed gas contains at least one dilute gas selected from the group consisting of steam, nitrogen, carbon dioxide, n-butane, isobutane and propane.

6. A process as claimed in any one of claims 1 or 2, wherein said feed gas contains 0.1 to 10 moles of steam per mole of isobutylene.

7. A process as claimed in any one of claims 1 or 2, wherein the amount of said molecular oxygen in said feed gas is in a range of from 0.4 to 5 moles per mole of isobutylene.

8. A process as claimed in any one of claims 1 or 2, wherein said catalyst is one prepared by uniformly mixing, in an aqueous medium, respective metal-containing compounds in the form of an oxide, salt or a mixture of said oxide and salt, by drying said mixture at a temperature not exceeding 300° C., by shaping said dried mixture, and by calcining said shaped mixture at a temperature of from 550° to 800° C.

9. A process as claimed in claim 8, wherein said drying operation is effected in two steps, in the first step of which, said mixture is heated at a temperature of from 100° to 150° C. and in the second step of which, said first dried mixture is heated at a temperature of from 150° to 300° C.

10. A process as claimed in claim 1, wherein the values of said subscripts b through g are in respectively the ranges of: b=4 to 10, c=1 to 5, d=0.5 to 4, e=0.001 to 0.3, f=0.05 to 1.5 and g=0.1 to 5.

* * * * *

UNITED STATES PATENT OFFICE
CERTIFICATE OF CORRECTION

Patent No. 4,217,309  Dated August 12, 1980

Inventor(s) Sumio Umemura, et al

It is certified that error appears in the above-identified patent and that said Letters Patent are hereby corrected as shown below:

Column 3, line 26: "Evenif" should be --Even if--.

Column 7, lines 43-44: "$[(NH_4)_6Mo_7O_{24}1.4H_2O]$" should be --$[(NH_4)_6Mo_7O_{24} \cdot 4H_2O]$--.

Column 13, Table 5: under column titled "Percent" and across from "Conversion of n-butene(*) insert --90.3--.

Table 6, columns 14 and 16: in the last column heading, "metharcrolein" should be --methacrolein--.

Signed and Sealed this

Twentieth Day of January 1981

[SEAL]

Attest:

RENE D. TEGTMEYER

Attesting Officer   Acting Commissioner of Patents and Trademar,